United States Patent [19]
De Pater et al.

[11] Patent Number: 5,840,940
[45] Date of Patent: Nov. 24, 1998

[54] LINOLEOYLAMIDE BASED CERAMIDE DERIVATIVE AND ITS USE IN COSMETIC PREPARATIONS FOR THE TREATMENT OF DRY SKIN

[75] Inventors: Robertus Mattheus De Pater; Hein Simon Koger, both of Delft; Johannes Wilhelmus Jacobus Lambers, Pijnacker; Jan Verweij, Leiden, all of Netherlands

[73] Assignee: Gist-Brocades B.V., Netherlands

[21] Appl. No.: 553,586

[22] PCT Filed: Mar. 20, 1995

[86] PCT No.: PCT/EP95/01069

§ 371 Date: Dec. 12, 1995

§ 102(e) Date: Dec. 12, 1995

[87] PCT Pub. No.: WO95/25716

PCT Pub. Date: Sep. 28, 1995

[30] Foreign Application Priority Data

Mar. 18, 1994 [NL] Netherlands ................. 94200712.1

[51] Int. Cl.$^6$ .................................................. C07C 233/00
[52] U.S. Cl. ............................................................ 554/61
[58] Field of Search ..................... 554/61, 68; 424/401; 514/547, 844, 847

[56] References Cited

U.S. PATENT DOCUMENTS 5,368,857  11/1994  Corcoran et al. .................... 424/401

FOREIGN PATENT DOCUMENTS

93/20038  10/1993  WIPO .......................... C07C 231/02

Primary Examiner—Gary Geist
Assistant Examiner—Deborah D. Carr
Attorney, Agent, or Firm—Bierman, Muserlian and Lucas

[57] ABSTRACT

The present invention discloses a novel ceramide 3 derivative which is N-linoleoylphytosphingosine (Ceramide IIIA). In addition, a method for preparing this compound is described. The solubility of this diunsaturated ceramide IIIA is much higher than the solubility of ceramide 1 and a saturated ceramide 3 compound. Compositions containing ceramide IIIA are described which are suitable for topical use. Furthermore, a method is given for maintaining the water permeability characteristics of the skin using compositions comprising ceramide IIIA.

1 Claim, 3 Drawing Sheets

LINOLEOYLAMIDE BASED CERAMIDE DERIVATIVE AND ITS USE IN COSMETIC PREPARATIONS FOR THE TREATMENT OF DRY SKIN

This application is a 371 of PCT/EP95/01069/ filed Mar. 20, 1995.

TECHNICAL FIELD

The present invention relates to a new physiologically active ceramide derivative. Specifically, the invention relates to a new linoleoylamide based ceramide. This ceramide is highly soluble in normally employed ceramide emollients. The bioavailability is increased and the ceramide is used for maintaining the epidermal water permeability barrier of the skin.

BACKGROUND OF THE INVENTION

It is generally understood that ceramides present within the intercellular lipid lamellae of the stratum corneum have an important structural function in the water permeability barrier of the skin. The ceramides are considered essential in maintaining said barrier. It is believed that one of the causes of a dry skin is a reduction in the amount of ceramides within these intercellular lipid lamellae. It is therefore desirable to be able to successfully replace these depleted lipids via the topical route.

Downing et al. (Arch. Dermatol. Res. 277, 284–287, 1985; J. Invest. Derm. 84, 410–412, 1985; J. Lipid Res. 24, 759–765, 1983) identified the six predominant existing types of ceramides in the stratum corneum. One of these types is characterized by the presence of linoleic acid in an ester linkage (so-called ceramide 1). Several references postulate that after hydrolysis this essential fatty acid plays an important role on its own in the hydration of the stratum corneum. (P. W. Wertz et al., Biochim. Biophys. Acta 753, 350– 355, 1983; P. Skolnik et al., Arch. Derm. 113, 939–941, 1977; P. Bowser et al., Biochim. Biophys. Acta 834, 429–436, 1985).

It is also observed that in surfactant-induced dry skin there exists a relative deficiency of a ceramide with phytosphingosine as a backbone (A. W. Fulmer et al., J. Invest. Derm. 86, 598–602, 1985). This ceramide was identified by Downing as ceramide 3. Ceramide 3 is a mixture of different molecules, characterized by the general name N-acylphytosphingosine, wherein the acyl group is saturated and has a chain length of 14 to 30 carbon atoms.

Ceramides must be able to penetrate the stratum corneum in order to reach the lipid lamellae of the permeability barrier. One of the unsolved problems with topical application of skin products is to find a suitable way to deliver the active ingredient in sufficient amounts to the place where it must exert its biological activity. The penetration of ceramides in the skin is highly dependent on their solubility in a cosmetic formulation.

KAO has disclosed in the European Patent Applications EP 227994 and EP 282816 that surfactants such as glycerylethers assist in penetration of ceramides into the stratum corneum. However, this kind of surfactants tend to permanently disrupt the stratum corneum so that afterwards the penetrated ceramide leaks out of the stratum corneum again.

A class of compounds with well known surfactant properties are fatty acids via acylation coupled with the aminoalcohol diethanolamine. It is observed that the surfactant properties improve with decreasing chain length and increasing degree of unsaturation of the fatty acyl group. (H. S. Vedanayagam et al., J. Oil Technol. Assoc. India, 15, 68–71, 1984).

In ceramide 3, a saturated fatty acid ($C_{14}$–$C_{30}$) is coupled via acylation with phytosphingosine. Phytosphingosine is also an aminoalcohol, but is structurally very different from diethanolamine. In contrast to diethanolamine, phytosphingosine already contains an alkyl chain (having a length of 14 carbon atoms in ceramide 3). The influence of the presence of this phytosphingosine alkyl chain on modifications in the acyl group of ceramide 3 cannot be predicted.

SUMMARY OF THE INVENTION

The invention provides a novel compound having the following structure:

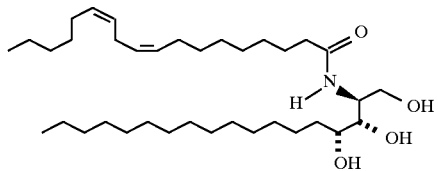

i.e. N-linoleoylphytosphingosine.

The invention further provides a method for preparing N-linoleoylphytosphingosine.

Compositions comprising the new compound are used for maintaining the integrity of the epidermal water permeability barrier of the skin. The compositions contain the new compound in an amount from 0.0001% to 25%, preferably from 0.005% to 5%, most preferably from 0.01 to 2% by weight of the composition.

The compound of the present invention can be used for therapy. In addition, the new compound can be used for cosmetics.

The present invention disloses a method for maintaining the water permeability characteristics of the skin characterized in that a formulation containing N-linoleoylphytosphingosine is applied topically.

DETAILED DESCRIPTION OF THE INVENTION

Figure 1:
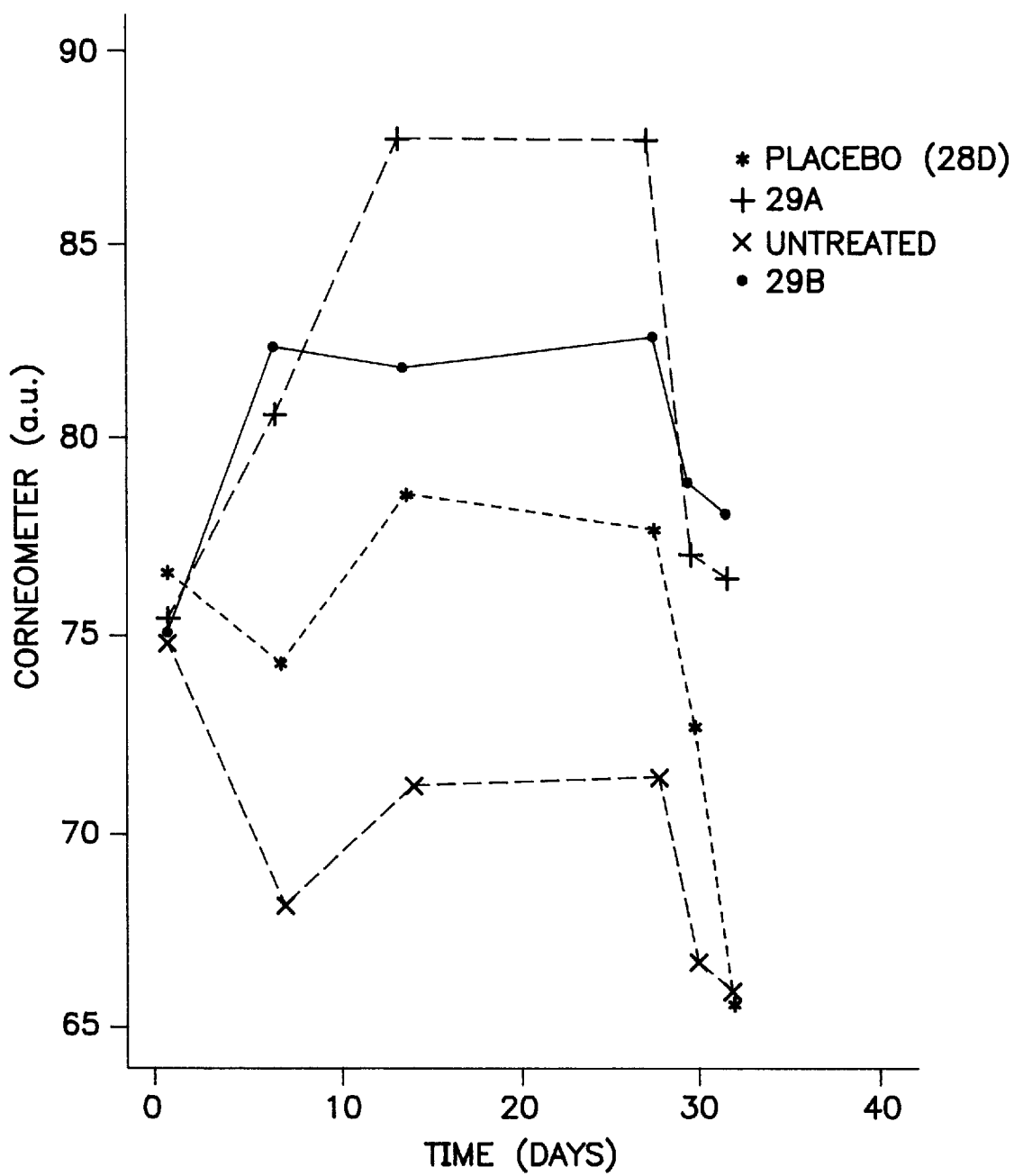
FIG. 1 shows multiple x-y plots of corneometer measurements on healthy skin, treated with ceramide 3 formulations and placebo.

The present invention provides a novel compound having the following formula:

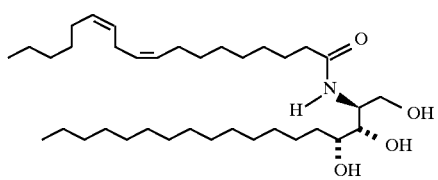

and identified as N-linoleoylphytosphingosine.

Linoleic acid is a diunsaturated C18 fatty acid. This fatty acid is an essential fatty acid. Ceramide 1 contains this fatty acid omega-esterified to a (long chain) fatty acid, whereby this whole side chain is linked via an amide linkage to sphingosine. When ceramide 1 is applied to the skin the linoleic acid is released due to the amidase and/or esterase activity naturally present in the skin and hence the acid is available to perform its function.

N-linoleoylphytosphingosine, the subject of the present invention, combines this skin-occurring advantageous fatty acid with the backbone of phytosphingosine. Phytosphingosine also is the backbone of ceramide 3. N-linoleoyl phytospingosine can be considered as a ceramide 3 derivative, in which the saturated fatty acyl group is substituted for a linoleoyl group, having two double bonds and 18 carbon atoms. This ceramide also is called ceramide IIIA.

The invention further provides a method for preparing N-linoleoylphytosphingosine. This ceramide IIIA may be prepared by various synthesic methods known to the skilled person, the choice of the synthesic method being not critical to the present invention.

The coupling between linoleic acid and phytosphingosine or a salt thereof can be carried out either enzymatically or chemically. Chemically, the acid can be coupled either as such using coupling reagents, e.g. EEDQ (N-ethoxycarbonyl-2-ethoxy-1,2-dihydroquinoline), HOBT (hydroxybenzotriazole) or a carbodiimide, or as an activated acid e.g. a mixed anhydride or acid halogenide.

An example of a chemical synthesis method is a method analogous to that of Mori and Nishio (1991) Liebigs Ann. Chem., 253–257. Another example is the method disclosed in International Patent Application WO93/20038.

Phytosphingosine is obtainable efficiently by deacetylation of tetra-acetylphytosphingosine (TAPS), which on its turn can be obtained in large amounts by microbial fermentation, especially by fermentation of *Hansenula ciferri*.

In another aspect of the invention it is disclosed that the new compound of the present invention is highly soluble in solvents containing fatty alcohol and esters and fatty acids, which can be used as emollients and which are accepted for use on the human skin. Examples of such solvents are: lauryl alcohol, cetyl alcohol, isocetyl alcohol, oleyl alcohol, stearoyl alcohol, isostearoyl alcohol, isostearic acid, isopropyl myristate, isopropyl stearate, cetyl palmitate, sugar- and glycol esters.

It is shown that ceramide 1 and ceramide III (a saturated ceramide 3 derivative with an acyl group of 18 carbon atoms) can be solubilised in isocetyl alcohol (Eutanol™ G16) and/or isostearic acid (Emersol) in an amount of less than 0.2% (w/v). In contrast, the ceramide IIIA of the present invention N-linoleoylphytosphingosine solubilises to an amount of 1% (w/v) or more in the indicated solvents.

The present invention further discloses cosmetic compositions containing ceramide IIIA.

The compositions comprising the new compound are used for maintaining the integrity of the epidermal water permeability barrier of the skin.

Specific cosmetic preparations include the usual components. The composition comprises a vehicle to enable the active ingredient to be conveyed to the skin. Vehicles include water, solids and liquids. These are classified as emollients, propellants, solvents, humectants, thickeners and powders.

Emollients include alkyl higher fatty acids, oils, and higher alcohols.

Propellants include propane, butane, isobutane, dimethyl ether, chlorofluoroalkanes, carbon dioxide, nitrous oxide.

Solvents include ethyl alcohol, methylene chloride, isopropanol, ethyl ethers, DMSO.

Humectants include glycerin, gelatin, sorbitol.

Powders include chalk, talc, starch, gums.

The vehicle additionnally contains specific agents that are able to interact with the stratum corneum to alter its natural resistance, the so-called penetration enhancers.

The present invention describes specific formulations which are able to target the ceramide to the proper site in the skin, i.e. the stratum corneum. The skin penetration enhancers should be present in the formulation to ensure proper targeting and, consequently, high efficacy of the ceramides. Various compounds can display a function as penetration enhancer, e.g. solvents and amphiphilic (surface active) compounds. Penetration enhancers include ethoxylated emulsifiers, such as Ceteareth-6 or Ceteareth-25.

The skin penetration enhancers further may be used in combination with an oil, such as a vegetable oil.

The combination of the said components can account for 10 to 99% of the composition.

The compositions containing the ceramide IIIA of the present invention are suitable for topical use. The amount of ceramide IIIA suitable for topical application ranges from 0.0001% to 25%, preferably from 0.005% to 5%, most preferably from 0.01 to 2% by weight of the composition.

The present invention disloses a method for maintaining the water permeability characteristics of the skin characterized in that a formulation containing N-linoleoyl phytosphingosine is applied topically.

By topical application of the ceramide IIIA of the present invention on surfactant-pretreated skin it is shown that the ceramide has a high capacity for restoration of the impaired lipid barrier of the skin. In addition, it is shown that ceramide IIIA has a clear moisture-retaining effect on healthy skin.

Example 1 provides a synthesis method for N-linoleoylphytosphingosine from its constituents phytosphingosine and linoleic acid, via acylation with a mixed anhydride of linoleic acid and a sulfonyl chloride.

Example 2 shows the solubility of N-linoleoylphytosphingosine (ceramide IIIA) as compared to the solubilities of a saturated ceramide 3 derivative (ceramide III) and ceramide 1.

On healthy skin, creams containing ceramide IIIA of the present invention (ceramide concentration 0.2 and 0.5%) were shown to produce a clear moisturizing effect compared to placebo (example 3).

Example 4 shows the effects of ceramide IIIA on SDS (sodium laurylsulphate)-damaged skin. After treatment of the skin with a 5% aqueous solution of SDS, a treatment period of 14 days with ceramide containing creams results in a quicker recovery of the barrier layer of SDS-treated skin than the placebo product. More specifically, a reduction of trans-epidermal water loss is observed, accompanied with an increase of skin humidity of damaged skin compared to placebo.

EXPERIMENTAL

Measurement Equipment

Skin Humidity

The corneometer CM 820 PC (Courage and Khazaka, Cologne, Germany) registers the electrical capacitance of the skin surface, which is a measure of the degree of moisture on the skin's surface. The capacitance is expressed digitally in arbitrary units (a.u.). Three measurements were performed on each test area and the mean was used to define hydration state of the stratum corneum.

The corneometer comprises a console and its sensor. The sensor is connected to the console by a special plug and coiled cable. The measurement is indicated on the 40×18 mm display screen on the console as a three-place number. The display also fulfils other information functions.

The sensor is rectangular in shape. Its special glass coated active front surface can be moved axially, and has a stroke of at least 3 mm. The measuring principle demands that the sensor surface be placed flat on the test object at a constant pressure. In order to ensure this as reproducibly as possible, the front surface of the measuring head has been designed to be very small (7×7 mm). The inner moveable part—the active front surface—is pressed against the skin by a spring using a force of 3.5N.

The corneometer is completely automatic in operation. In order to carry out a measurement, the measuring head is pressed against the area of skin to be measured. The measured value is displayed after one second.

Trans-epidermal Water Loss

Measurements of trans-epidermal water loss (TEWL) were performed with the Tewameter (Courage & Khazaka, Cologne, Germany). The Tewameter is a device for measurement of water evaporation on skin surfaces based on the diffusion principle discovered by A. Fick in 1885.

EXAMPLE 1

A Method for Preparing N-linoleoylphytosphingosine

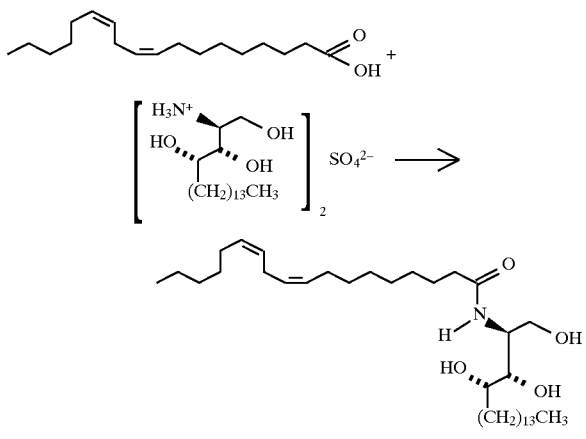

From a suspension of phytosphingosine sulphate (84.02 g) in ethyl acetate (800 ml), ethyl acetate (500 ml) was distilled off, after which triethyl amine (50 ml) was added to the suspension.

In a separate flask a solution of linoleic acid (86.2 g; purity 65%) and triethyl amine (100 ml) in ethyl acetate (160 ml) was added to a solution of p-toluenesulfonyl chloride (54.23 g) in ethyl acetate (425 ml) with stirring at 40° C. during 30 minutes. After stirring for another 30 minutes at 43° C. this mixture, containing the mixed anhydride of linoleic acid and p-toluenesulfonyl chloride, was added to the stirred mixture of phytosphingosine sulphate, triethyl amine and ethyl acetate during 20 minutes. The flask that contained the mixed anhydride was rinsed with 50 ml ethyl acetate.

After stirring for about 1 hour at 43° C. 400 ml of water was added to the reaction mixture and the pH was adjusted to 6.8 with a HCl solution (37 %). Then the layers were separated and the organic layer was washed again with 400 ml of water of which the pH was adjusted to 2.1 with a HCl solution (37%). After washing the ethyl acetate layer with 100 ml of a NaCl solution (10% in water), 500 ml of ethyl acetate was removed by distillation. During washings and separations the temperature was kept at about 45° C.

After adding ethyl acetate (500 ml) the mixture was filtrated at about 45° C. and cooled down slowly to 3° C. The crystalline precipitate formed was filtered off, washed with cold methanol (250 ml) and dried in vacuo giving 91.89 g of N-linoleoylphytosphingosine.

PMR-spectrum (360 MHz; $CDCl_3/CD_3OD$ v/v 1:1; values in ppm; δ $CH_3OH$ 3.23).

δ: 0.80 (t, 3H); 1.1–1.7 (m, 44H); 1.94 (m, 2H); 2.14 (t, 2H); 2.65 (m, 2H); 3.46 (m, 2H); 3.66 (dABq, 2H); 4.00 (m, 1H); 5.26 (m, 4H).

EXAMPLE 2

Solubility of the N-linoleoylphytosphingosine

The compound produced in Example 1, N-linoleoyl phytosphingosine was tested by solubilisation in isocetyl alcohol (Eutanol™ G16, Henkel) and isostearic acid (Emersol, Henkel).

Increasing amounts of the compound were added to the solvent and stirred under nitrogen for 30 minutes at 45° C. After cooling to room temperature (22°±2° C.) the solutions were kept in the dark. After 1, 24 and 48 hours the solutions were visually inspected. The maximum concentration was determined before the solution turned cloudy, indicating the presence of insoluble crystals.

The solubilities of a saturated ceramide 3 derivative, N-stearoylphytosphingosine (ceramide III), and of ceramide 1 were also determined. The results are shown in Table 1.

It can be seen that N-linoleoyl phytosphingosine solubilizes much better than its saturated analogue and than ceramide 1.

TABLE 1

Solubility of ceramide 3 derivatives and ceramide 1

| | (% w/v) | | |
|---|---|---|---|
| EMOLLIENT | CERAMIDE III | CERAMIDE IIIA | CERAMIDE 1 |
| Isocetyl alcohol | 0.16 | 5 | <0.1 |
| Isostearic acid | 0.06 | 1 | nd |

Ceramide III N-stearoylphytosphingosine
Ceramide IIIA N-linoleoylphytosphingosine
nd: not determined

EXAMPLE 3

Long-term Effects of Ceramide IIIA on Healthy Skin

| Formulations tested O/W-Emulsion with Ceramide IIIA | | | |
|---|---|---|---|
| | 29A | 29B | 28D |
| Ceteareth-6 (and) stearyl alcohol | 3.25 | 3.25 | 3.25 |
| Ceteareth-25 | 1.75 | 1.75 | 1.75 |
| Caprylic/capric triglyceride | 3.00 | 3.00 | 3.00 |
| Stearyl Beeswaxate | 1.00 | 1.00 | 1.00 |
| Decalyceryl pentaisostearate | 5.00 | 5.00 | 5.00 |
| Cetyl alcohol | 2.50 | 2.50 | 2.50 |
| Avocado Oil | 5.00 | 5.00 | 5.00 |
| Octyl stearate | 2.00 | 2.00 | 2.00 |

-continued

Formulations tested
O/W-Emulsion with Ceramide IIIA

|  | 29A | 29B | 28D |
|---|---|---|---|
| Dioctylcyclohexane | 3.00 | 3.00 | 3.00 |
| Ceramide IIIA | 0.50 | 0.20 | 0.00 |
| Preservative* | 0.50 | 0.50 | 0.50 |
| Water | 72.50 | 72.80 | 73.00 |
| Total | 100.00 | 100.00 | 100.00 |

*propylene glycol (and) phenoxyethanol (and) methylparaben (and) propylparaben (and) ethylparaben (and) butylparaben Time of Evaluation before treatment 2 hours after last application on days 7, 14, 28 four days after application was ceased

Test Method

Five female volunteers at the age of 28–40 years with healthy skin were included in the test.

Measurements were carried out at a temperature of 22°±1° C. and a relative humidity of 60±10%. Subjects were accustomed to ambient conditions for 20 min prior to any measurement. The test was carried out on the volar forearms. Initially untreated skin was measured in all three areas to find baseline values. After measuring the three test products were applied, one area remained untreated. The dose of application was about 2 mg/cm$^2$. In the following 28 days a home application in the morning and evening took place.

Measurements were evaluated during the treatment period on day 7, 14 and 28 two hours after the last daily application. The application was ceased on day 28 and further measurements were evaluated on day 30 and 32. Use of other cosmetic products was restricted on the test areas throughout the whole study.

Results

Moisturing Effect

Summary statistics (Statgraphics Plus Version 6, Manugistics U.S.A.) procedure was used to determine the center, spread, and shape of the data. The system performs the following calculations: average, median, variance, standard deviation, standard error, minimum and maximum. FIG. 1 shows the mean results in multiple x-y plots.

The ceramide containing creams (0.2%, 0.5%) gave clear effects compared to placebo. With two daily applications the maximal effect was achieved after around 14 days and then remained nearly constant throughout the further application period. Two and four days after the last application the humidity of the skin was still significantly increased compared to placebo and untreated area.

Conclusion

The ceramide containing products gave clear moisturizing effects compared to placebo.

Thus, the effect of ceramide containing preparations in enhancing the properties of the stratum corneum with respect to its water retaining function is proved in this example.

EXAMPLE 4

Effects of Ceramide IIIA on SDS-damaged Skin

Formulations Tested

See Example 3.

Time of Evaluation after damaging the skin with SDS 1 hour after last application on days 3, 7, 14

Test Method

Five female volunteers at the age of 22–43 years with healthy skin were included in the test.

Measurements were carried out at a temperature of 22°±1° C. and a relative humidity of 60±10%. Subjects were accustomed to ambient conditions for 20 min prior to any measurement. The test was carried out on the volar forearms. The skin of the forearms was treated with a 5% aqueous solution of sodium lauryl sulphate (SDS) and an occlusive dressing applied. The dressing was removed 2 h later, and the regions gently washed with water and air-dried. After 30 min the measurements were done. Then the three test products were applied, one area remained untreated. The dose of application was about 2 mg/cm$^2$. In the following 14 days a home application in the morning and evening took place.

Measurements were evaluated during the treatment period on day 3, 7 and 14 one hour after the last daily application. Use of other cosmetic products was restricted on the test areas throughout the whole study.

Results

Moisturing Effect

Figure 2:
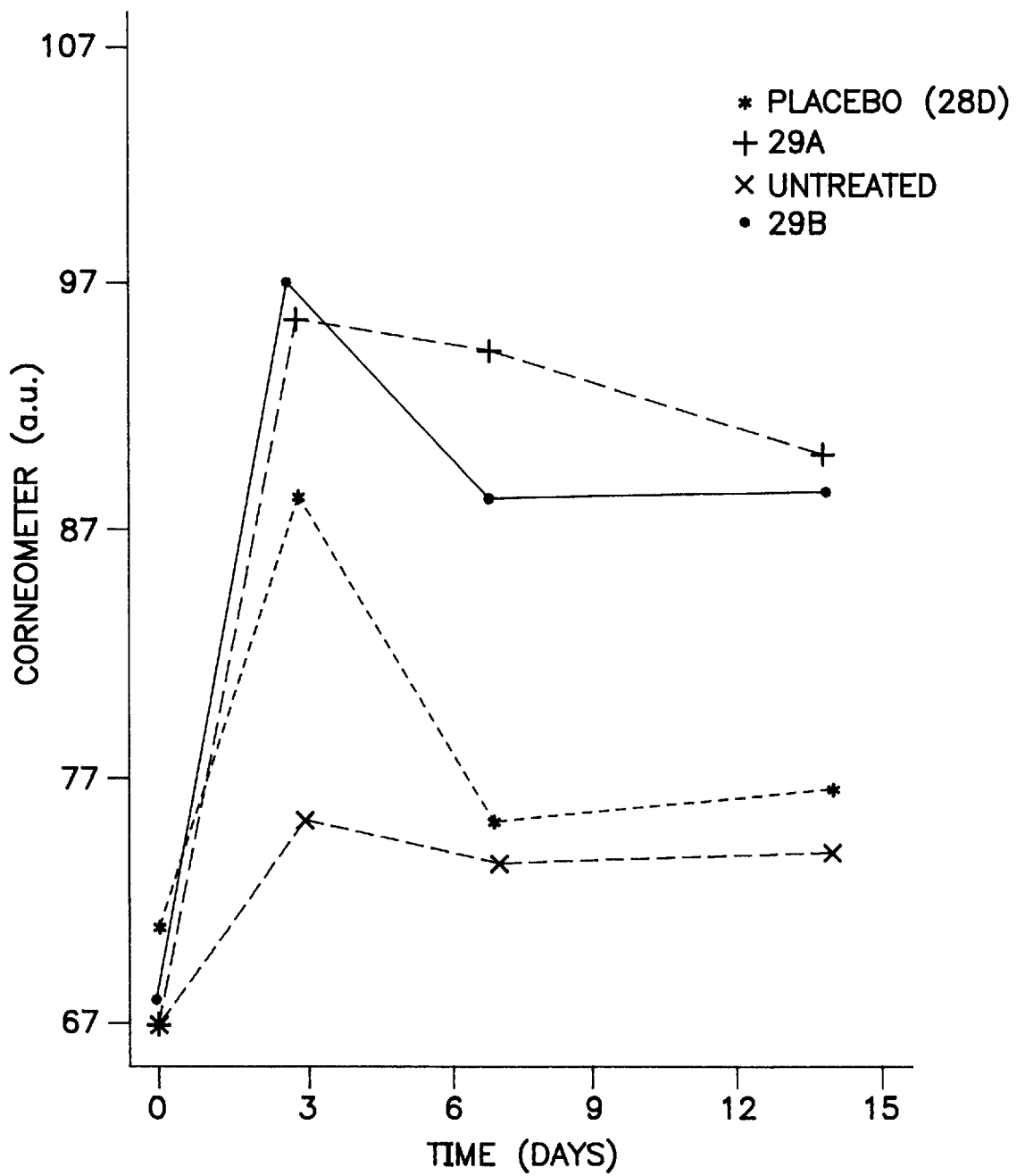
FIG. 2 shows multiple x-y plots of corneometer measurements on SDS-damaged skin, treated with ceramide 3 formulations and placebo.

Summary statistics (Statgraphics Plus Version 6, Manugistics U.S.A.) procedure was used to determine the center, spread, and shape of the data. The system performs the following calculations: average, median, variance, standard deviation, standard error, minimum and maximum. FIG. 2 shows the mean results in multiple x-y plots.

The ceramide containing creams (0.2%, 0.5%) gave clear effects compared to placebo. With two daily applications the maximal effect was achieved after around 7 days.

TEWL

Figure 3:
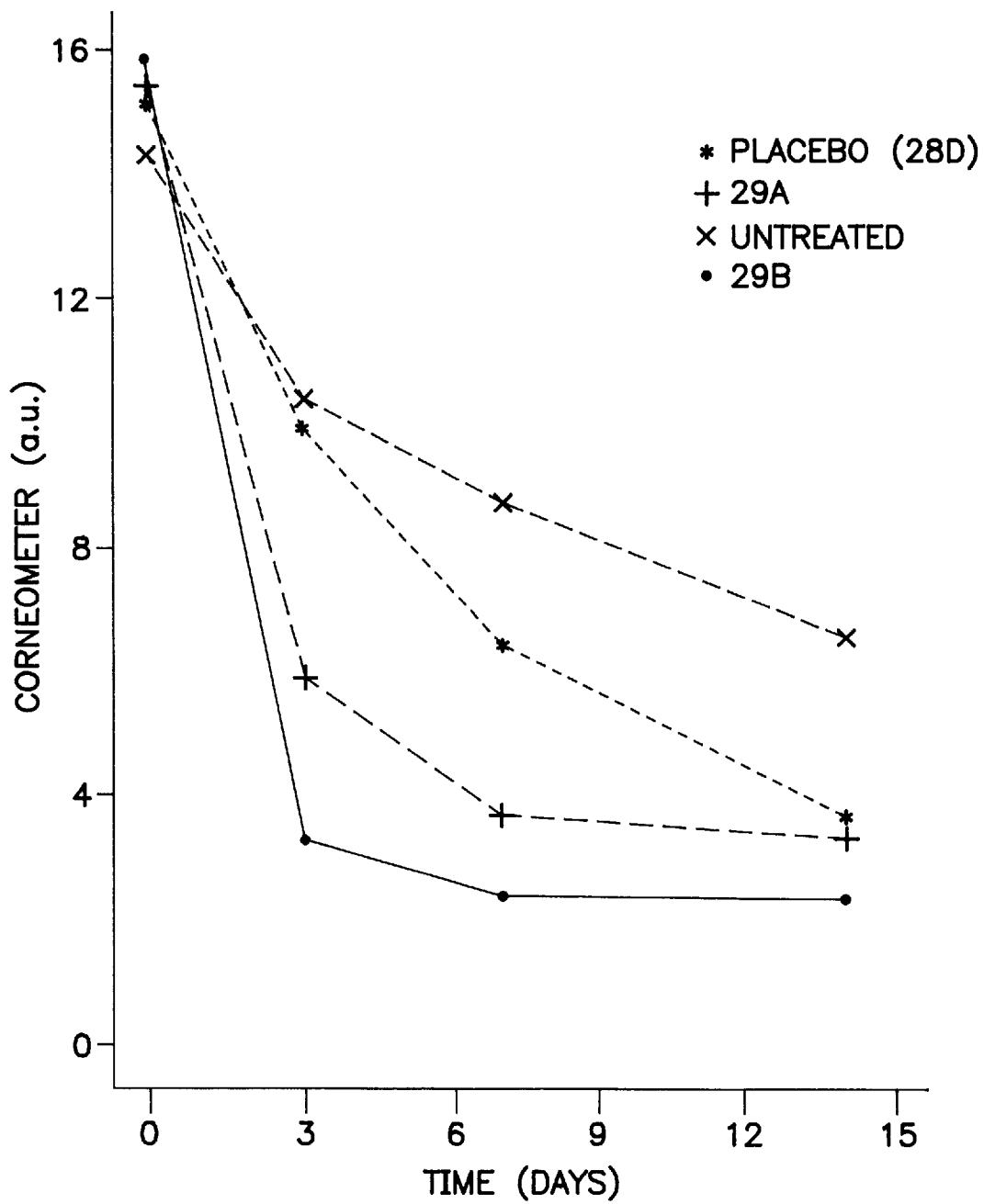
FIG. 3 shows multiple x-y plots of TEWL measurements on SDS-damaged skin, treated with ceramide 3 formulations and placebo.

FIG. 3 shows the mean results in multiple x-y plots. The ceramide containing products normalize the TEWL in a shorter time (only three days) than the placebo product (nearly 14 days). The TEWL in the untreated area takes more than 14 days to return to normality. There are no different effects on the regeneration process between the ceramide IIIA containing formulations.

Conclusion

A treatment period of 14 days with the ceramide containing creams produced a reduction of TEWL, accompanied with an increase of skin humidity of damaged skin compared to placebo.

Thus, the ceramide containing preparations lead to a quicker restitution of the barrier layer of SDS-damaged skin than the placebo product.

We claim:

1. A compound having the formula:

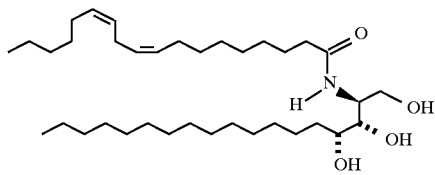

which is N-linoleoylphytosphingosine.

* * * * *